(12) United States Patent
Hancock (10) Patent No.: US 6,423,090 B1
(45) Date of Patent: Jul. 23, 2002

(54) STENT PATTERN WITH STAGED EXPANSION

(75) Inventor: David Hancock, San Francisco, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/503,107

(22) Filed: Feb. 11, 2000

(51) Int. Cl.7 .................................................. A61F 2/06
(52) U.S. Cl. ...................................................... 623/1.15
(58) Field of Search .............................. 623/1.11, 1.15, 623/1.12, 1.16, 1.13; 606/198, 191, 195

(56) References Cited

U.S. PATENT DOCUMENTS

| | | | |
|---|---|---|---|
| 5,449,373 A | * | 9/1995 | Pinchasik et al. .......... 623/1.11 |
| 5,766,238 A | * | 6/1998 | Lau et al. .................... 606/198 |
| 5,814,063 A | | 9/1998 | Freitag |
| 5,827,321 A | | 10/1998 | Roubin et al. |
| 5,840,081 A | | 11/1998 | Andersen et al. |
| 5,855,601 A | | 1/1999 | Bessler et al. |
| 5,876,432 A | * | 3/1999 | Lau et al. ................... 623/1.15 |
| 5,922,020 A | | 7/1999 | Klein et al. |
| 5,922,021 A | | 7/1999 | Jang |
| 6,146,403 A | | 11/2000 | St. Germain |
| 6,183,507 B1 | | 2/2001 | Lashinski et al. |
| 6,190,405 B1 | | 2/2001 | Culombo et al. |
| 6,190,406 B1 | | 2/2001 | Duerig et al. |

FOREIGN PATENT DOCUMENTS

| | | |
|---|---|---|
| WO | WO 99/36002 | 7/1999 |
| WO | WO 99/62430 | 9/1999 |

* cited by examiner

*Primary Examiner*—Kevin T. Truong
(74) *Attorney, Agent, or Firm*—Fulwider Patton Lee & Utecht, LLP (57) ABSTRACT

A medical device including structure for accomplishing staged expansion. The staged expansion of the medical device operates to reduce actual shortening during expansion as well as potential trauma to a repair site during implantation. In a preferred embodiment, the medical device is intended to be used in conjunction with a delivery catheter with an expandable portion adapted to radially expand the medical device.

18 Claims, 7 Drawing Sheets

STENT PATTERN WITH STAGED EXPANSION

BACKGROUND OF THE INVENTION

The present invention relates to a medical device and more particularly to a stent for use with an expandable device for repairing diseased blood vessels.

The vasculature of an animal or a human characteristically suffers from a variety of maladies. Vessel walls can weaken and become distended over time in response to blood flow and pressures, thereby resulting in formation of aneurysms. Such aneurysms can take on a myriad of forms. In particular, aneurysms may form at or near bifurcated vessels creating enlarged areas about the bifurcation, or may form a pocket, for example, in side walls of vessels. Due to the complications associated with aneurysms that rupture or otherwise fail, it is critical that an aneurysm be treated expeditiously and effectively. Intravascular treatment procedures include placing grafts within the aneurysm in a manner to ensure that blood flows through the graft rather than through the weakened vessels. Grafts are sometimes anchored at the repair site using expandable stents, precise placement of which is often highly desirable.

Moreover, aneurysms in the form of pockets in the sidewall of a vessel may be repaired using stents. In the event such an aneurysm is formed in a patient's vasculature, the pocket defined by the aneurysm might first be segregated from the parent vessel by placing a stent across the aneurysm neck, and then filling the aneurysm with embolic material. The stent limits flow of blood into the aneurysm and prevents embolic material from herniating into the parent vessel. Again, precise placement of the stent is often highly desired.

Stenoses also typically form in vasculature of humans and animals. Specifically, thrombotic or atherotic stenoses can form nearly anywhere in the vasculature. Such narrowing of the vessel is, of course, highly dangerous to the patient where the afflicted vessel provides the sole blood flow access to critical parts of the body. To treat such stenoses, a supporting structure can be placed at the diseased site for the purpose of enlarging and holding open the vessel. It is known in the art to employ stents for this purpose.

Various means have been provided to deliver and implant stents for the purpose of facilitating the repair of narrowed or weakened vessels. One method frequently described for delivering a stent to a desired intraluminal location includes mounting the expandable stent on an expandable member, such as a balloon, provided on the distal end of an intravascular catheter. The assembly is then advanced to the desired location within the patient's body lumen, the balloon on the catheter is expanded to open the stent into a permanent expanded condition and then the balloon is deflated and the catheter removed from the vasculature.

It has become desirable to perform such procedures in the cerebral vasculature to open vessels that are narrowed by fibrins, platelets, plaque or calcium or to reinforce weakened vessels such as those suffering from aneurysms. Due to the threat of stroke and the need to maintain bloodflow to the brain, it is particularly desirable to treat such vessel abnormalities as expediently and effectively as possible. Since cerebral vasculature is characterized by having numerous perforators branching from main pathways and since such perforators often provide the only blood source to a particular part of the brain, accurate placement of the stent within cerebral vasculature is highly critical. Unfortunately, stents often move longitudinally within the vessel during expansion, often resulting in inaccurate placement.

Furthermore, many conventional stents shorten when they expand from a contracted state to an expanded state. Such shortening often occurs due to forces applied by the catheter used in deployment. In particular, the balloon portion of a balloon catheter, upon expansion, can generate inwardly directed loads upon the ends of the stent thereby causing the stent to shorten in length. This shortening is typically variable and difficult to quantify reliably which adversely effects the accurate placement of the stent within vasculature.

Additionally, expansion of the stent can itself be traumatic to a vessel wall. That is, uncontrolled expansion can result in the stent forcefully engaging and thereby damaging a vessel wall. Thus, a high rate of expansion of the stent may be undesirable.

Accordingly, what is needed is a stent that can be accurately placed within vasculature and that can be repositioned at some intermediate stage of expansion that is less than the final expanded size but greater than the original reduced size. It is also desirable that the stent embodies structure that offsets the shortening of the stent due to balloon expansion forces. Controlled expansion of the stent is also desirable. The present invention satisfies these needs.

SUMMARY OF THE INVENTION

Briefly, and in general terms, the present invention provides a medical device that includes structure that is adapted to minimize the effect of opposing forces typically applied by expandable members of a delivery catheter. The medical device of the present invention also includes structure that facilitates staged expansion of the stent.

In a preferred embodiment, the medical device embodies a stent that has a generally overall tubular configuration. The stent body is defined by a pattern of repeating and symmetrical beam elements that share a common longitudinal axis. In a preferred configuration, the repeating beam elements form an annular element embodying a circumferentially directed wave form. The beam elements can also form a helical pattern. The beam elements are characterized by including low force actuated beams and high force actuated beams. Through variance of dimensions of the two types of beam elements, full expansion of the low force elements can be achieved prior to expansion of the high force elements, resulting in a staged expansion characteristic of the stent.

The present invention also provides a stent which expands in a more controlled fashion. Specifically, the contemplated stage expansion reduces the rate of expansion of the stent of the present invention, thereby facilitating the minimization of the forces applied to the wall of a target vessel characteristic to uncontrolled expansion. Additionally, the staged expansion facilitates repositioning of the device at an intermediate stage of expansion.

It is to be recognized that as the low force actuated beams are deflected, the force required to continue deflection increases. Eventually, the force required is great enough to begin deflecting the large force actuated beams. At this point, a second phase of expansion begins. By varying the number and quality of the high and low force actuating beams, a desired stage expansion and rate of expansion is achieved.

These and other objects and advantages of the invention will become apparent from the following more detailed description, when taken in conjunction with the accompanying drawings of the illustrated embodiments.

DETAILED DESCRIPTION OF THE PREFERRED EMBODIMENTS

Figure 1:
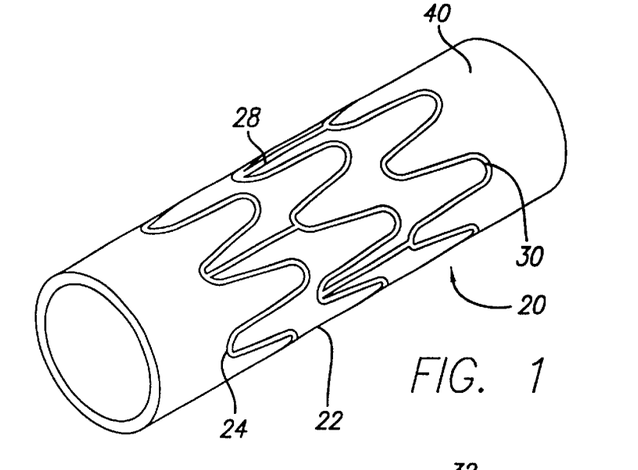
FIG. 1 is a perspective view of a medical device of the present invention shown mounted on a mandrel.
Figure 2:
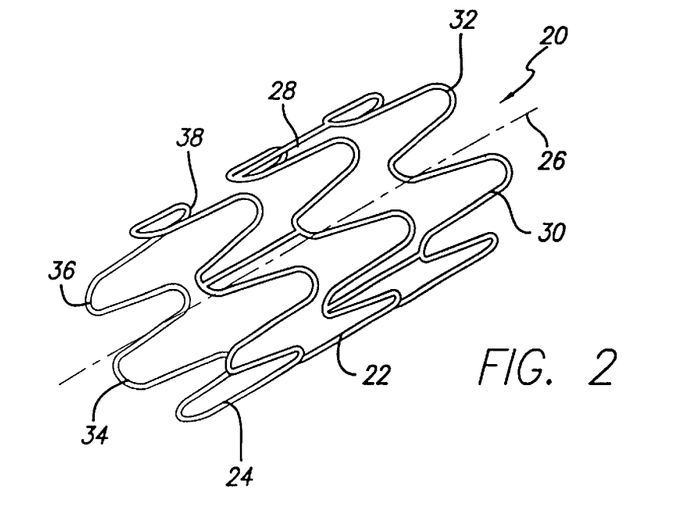
FIG. 2 is a perspective view of the medical device of FIG. 1 removed from the mandrel.

Referring now to the drawings, and in particular, FIGS. 1 and 2, there is shown a repair device of the present invention. The medical device is characterized by embodying structure which facilitates offsetting opposing forces applied thereto when the device is being deployed within vasculature. Specifically, the medical device includes structure that enables it to be expanded in stages, such expansion additionally having the benefit of providing enhanced control and reducing impact forces generated during deployment.

The medical device of the present invention is embodied in a stent 20 having a stent body 22. The stent body 22 defines a generally tubular configuration and includes a plurality of annular elements 24 that share a common longitudinal axis 26. The annular elements are connected to each other by at least one generally longitudinally extending strut 28. Such struts 28 can be arranged in a line or may occupy different circumferential positions about the stent body 27. Additionally, the struts 28 between adjacent annular elements 22 may number as many as eight (8).

Each annular element 24 is characterized by circumferentially directed serpentine pattern 30. The serpentine pattern 30 winds its way about a circumference of the stent body 22. The serpentine pattern 30 is further characterized by including a plurality of proximally directed peaks 36 as well as distally directed peaks 38. The stent body 22 additionally includes a superior or distal end 32 and an inferior or a proximal end 34. The connecting struts 28 may be attached between a proximally directed peak 36 of one annular element 24 to a distally directed peak 38 of an adjacent annular element 24. Alternatively, struts 28 may additionally be positioned anywhere between adjacent annular elements 24.

In a presently preferred embodiment, the stent 20 is contemplated to be cut from a tube employing conventional means such as a laser. More specifically, the tube (not shown) would be placed on a mandrel 40 and the desired stent pattern cut into the tube. The excess tube material would be discarded and the mandrel 40 removed from the resultant stent. It is also contemplated that the medical devices of the present invention be cut from a tube having variable thickness. To wit, the resultant beams defining the device can be manufactured with variable thickness and deflection responses. As such, a low force beam 46 can be made thinner than a high force beam 44.

Figure 3:
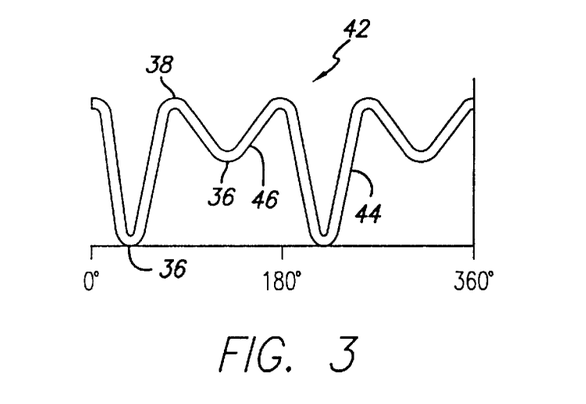
FIG. 3 is a side view of one embodiment of an annular element of the medical device of the present invention, depicting the annular element in a sectioned and flattened state.

With reference to FIG. 3, an exemplar of one presently preferred stent pattern 42 includes large force actuated beams 44 and small force actuated beams 46. This stent pattern 42 includes an alternating series of two small force beams 46 and two large force beams 44. It is to be recognized that although the figures depict a stent 20 including a series of three annular elements, as few as one annular element and as many as twenty or more annular elements are contemplated. It is also to be recognized that the radius of curvature of the peaks 36, 38 and the large and small force beams 44, 46 themselves can be varied for a particular purpose. In particular, beam length, width, thickness, material, straightness and orientation can be varied. Irrespective of such dimensional criteria, the resultant staged expansion of the stent 20 remains as the desired goal.

Figure 4:
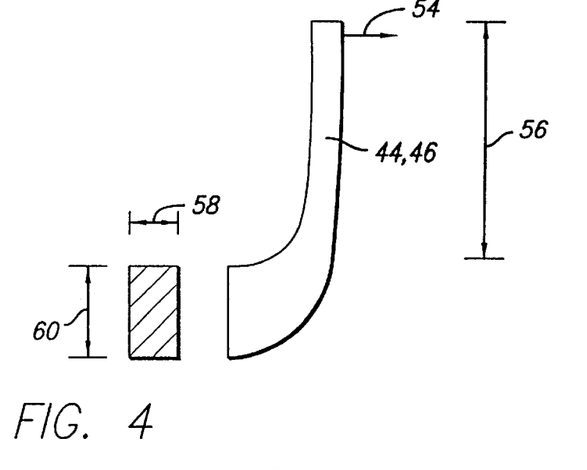
FIG. 4 is a schematic representation, partially in cross-section, of an undeflected member defining a waveform of an annular element of the medical device of the present invention.
Figure 5:
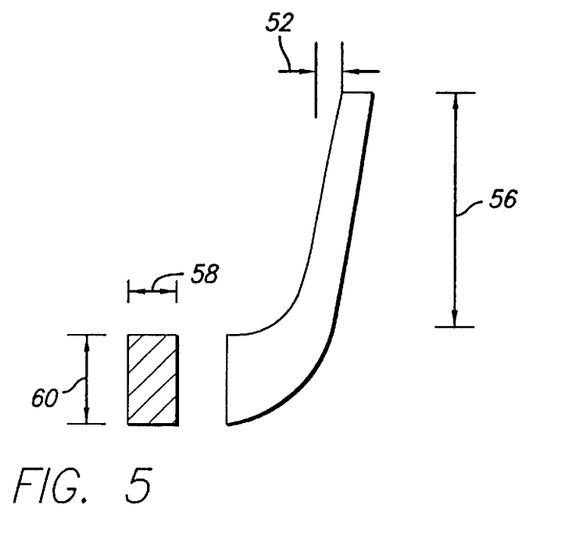
FIG. 5 is a schematic representation, partially in cross-section, depicting the member shown in FIG. 4 after deflection.

It is contemplated that to alter the expansion of the annular elements 42 and to accomplish staged expansion, the cross-sectional profiles of the large force 44 and small force 46 beams are modified. Such members 44, 46 perform according to a cantilever beam theory. That is, with reference to FIGS. 4 and 5, the amount of deflection 52 relates to a specific load or force 54 according to the following relationship:

$$\text{Deflection} = \frac{\text{Force} \times (\text{Length of Moment Arm})^3}{(\text{Modulus of Elasticity}) \times (\text{Moment of Inertia})}$$

where the length of the moment arm 56 can be varied and the modulus of elasticity is dependent upon the material of the moment arm 56. The moment of inertia is dependent upon the thickness 58 and width 60 of a cross-sectional profile (though rectangular, oval and circular profiles are contemplated) of the members 44, 46 according to the following relationship:

$$\text{Moment of Inertia} = \frac{\text{Thickness} \times \text{Width}^3}{12}$$

Accordingly, for a given force, the magnitude of deformation 52 can be controlled, for example, by varying the length of a members 44, 46 as well as its thickness 58 and width 60 at points along the length as well as material composition.

Figure 6:
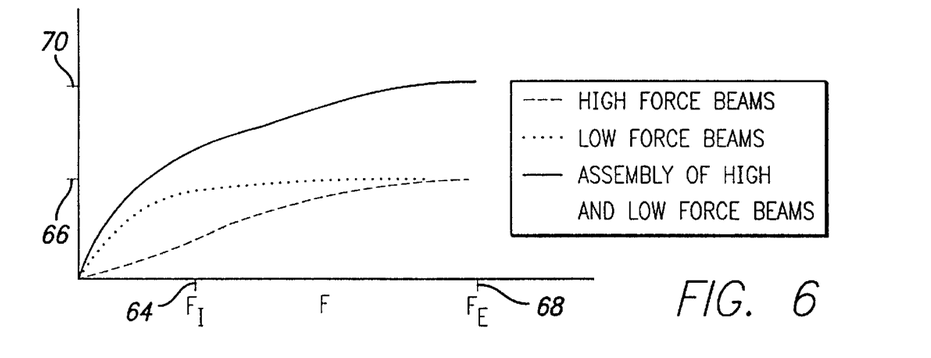
FIG. 6 is a graphical representation, depicting a composite-force deflection graph.

With reference to FIG. 6, a general discussion of the force-deflected characteristics of a beam is provided. As a force $F_I$, 64 is applied to a beam, the beam deflects. Initially, little force is required to achieve a deflection. As the beam deflects, the moment arm begins to decrease and more force is required to continue the deflecting action. Eventually, very large increases in force $F_E$ 68 are required to achieve small deflections. This behavior describes a curve. The curve can be modified by varying the length, cross-section, and material of a particular beam. The behavior of a series of beams can be construed by adding the effects of the individual beams. Beams of high force and low force then can be assembled as desired to create a staged expansion profile. Generally, what is desired is a rapid early expansion to a diameter 66 at a relatively low force 64. Slow growth then occurs at higher forces until the final size 70 is achieved. This growth profile still achieves the desired effects of slower stent growth at higher pressures, positional readjustment, and minimal shortening.

Although a two-staged expansion has heretobefore been described, a three or more staged expansion is also contemplated. To achieve a three stage expansion, for example, three different force beams would be included in a stent pattern, each beam deflecting different amounts in response to an identical force.

To wit, a first expansion could be achieved in response to a first expanding force. Thereafter, a second expansion diameter would be achieved in response to a second relatively higher force and a final expanded diameter being accomplished by continuing to increase the force being applied.

Figure 7:
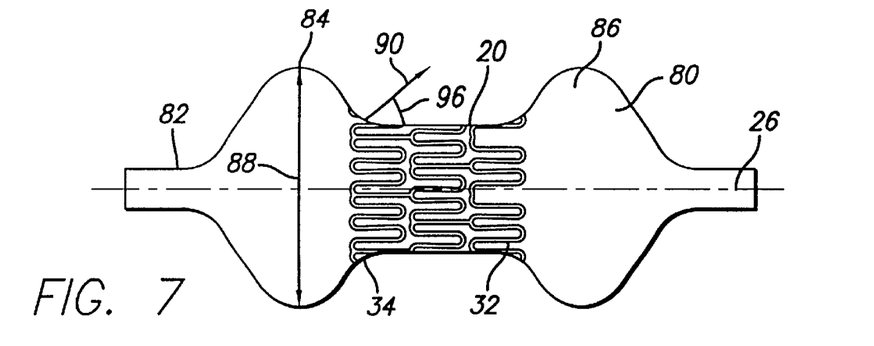
FIG. 7 is a side view of a medical device of the present invention mounted on a balloon, depicting the medical device in a crimped state.
Figure 8:
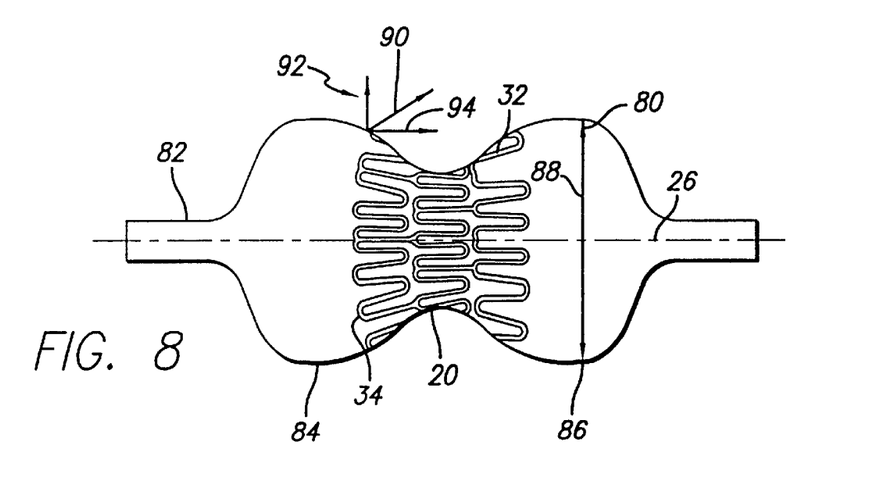
FIG. 8 is a side view depicting an initial expansion of the system shown in FIG. 7.
Figure 9:
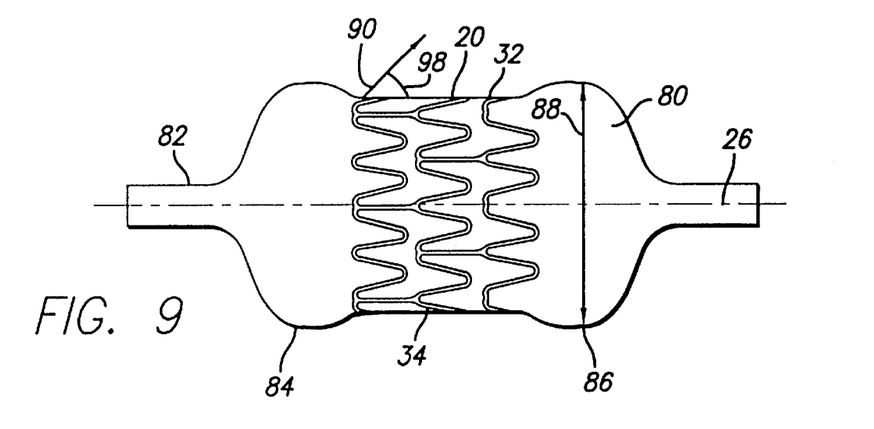
FIG. 9 is a side view of the system shown in FIGS. 7 and 8, depicting the medical device of the present invention in an intermediate expanded condition on a balloon.

As stated, one advantage of staged expansion of the stent 20 of the present invention, is that the degree of stent 20 shortening can be reduced. That is, the stent 20 of the present invention includes structure that offsets inwardly directed forces applied to the ends 32, 34 of the stent 20 by an expandable member of a delivery catheter. In addition, the stent 20 of the present invention, due to its staged expansion, facilitates repositioning of the stent 20 when it is in its intermediate expansion state. With reference to FIGS. 7–9, the forces generated through balloon expansion will now be explained.

In a typical delivery procedure, a stent 20 is mounted in a crimped condition on a balloon 80 of a delivery catheter 82. The assembly is then introduced into a patient's vasculature using conventional means such as the Seldinger technique and advanced within the vasculature until the repair site is reached. At the repair site, the balloon 80 is expanded which operates to expand the stent 20 into engagement with the vessel wall at the target site. The balloon 80 is then deflated and removed from the vasculature leaving the stent 20 implanted at the repair site.

Conventional balloons 80, however, do not expand in a uniform manner. Rather, a conventional balloon 80 tends to fully expand at its proximal 84 and distal 86 end portions to a final diameter 88 thereby forming shoulders, while a middle portion 90 upon which the stent is mounted, expands more slowly. It is, of course, the radial strength of the stent 20 itself that causes the middle portion 90 of the balloon 80 to assume a reduced diameter until the stent 20 is expanded.

Such expansion of a balloon 80 results in the inwardly directed or opposing forces on the ends 32, 34 of the stent 20. Generally speaking, as the balloon 80 of the delivery catheter 82 expands, a force 90 is generated at an orthogonal angle to the surface of the balloon. This force comprises a radially directed component 92 and longitudinally directed component 94.

It is to be recognized that a portion of the balloon 80 that is expanded at a perpendicular angle to a longitudinal axis 26 of the stent 20, solely comprises a radially directed component 92 of the force generated by the balloon, and no longitudinally directed component 94. Likewise, a portion of the balloon 80 that expands at an angle parallel to the longitudinal axis 26 of the stent 20, though unlikely, solely comprises a longitudinally directed force component 94.

The radially directed component 92 of the force operates on the entire circumference and length of the stent 20 and tends to open the stent 20 from its compressed condition to its expanded configuration. Unfortunately, the longitudinally directed component 94 of the force, such force being applied at both ends of stent 20 and about its entire interior circumference, operates to axially compress the stent 20.

It is further to be recognized that when the stent 20 is in its fully crimped state as shown in FIG. 7, the force being applied to the stent 20 by the balloon is at a relatively acute angle 96 to the ends of the stent 20. Such forces comprise a relatively higher longitudinal component 94. In contrast, when the stent reaches an intermediate expanded condition as shown in FIG. 9, the forces generated by the balloon 80 is at a relatively larger acute angle 98 to the ends of the stent 20.

These relatively larger acute angle forces 98 comprise a relatively smaller longitudinal component 34 of the force 90 applied by the balloon 80. Thus, by minimizing the exposure of the stent 20 to the relatively larger longitudinal component of forces 94, the amount of axial shortening can be reduced.

Figure 10:
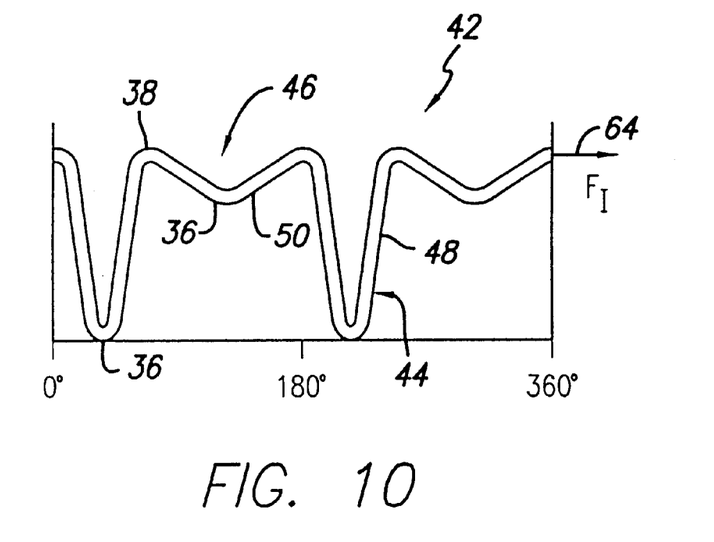
FIG. 10 is a side view of the sectioned annular element depicted in FIG. 3 after an initial expansion.
Figure 11:
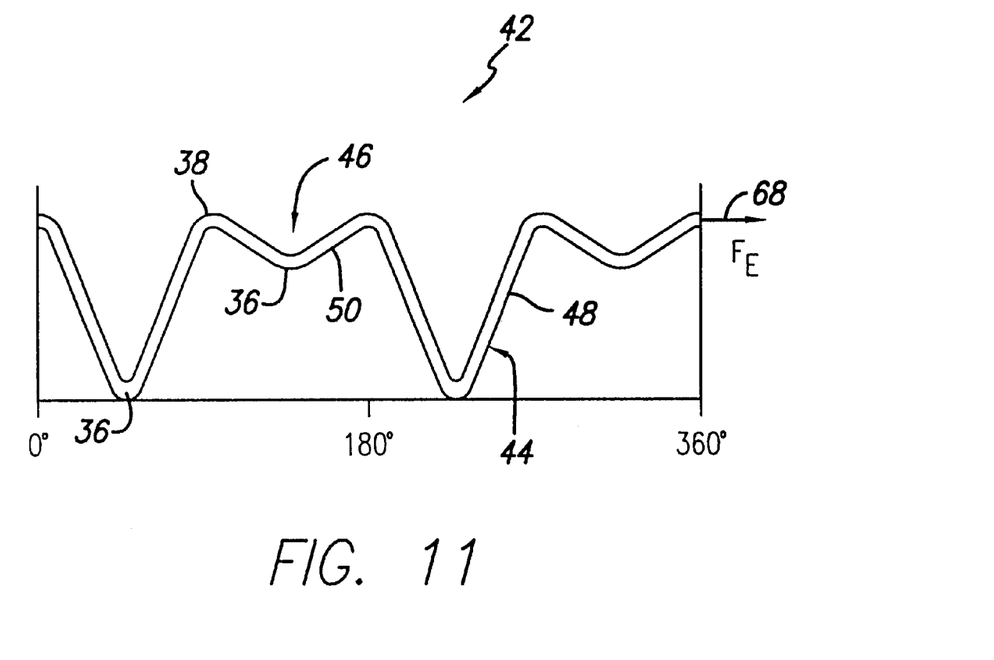
FIG. 11 is a side view of the sectioned annular element of FIG. 10 in a more fully expanded condition.

Turning now to FIG. 3 and FIGS. 10 and 11, there is shown an example of the dynamics involved in the staged expansion of the stent 20 of the present invention. As previously stated, in order to achieve staged expansion, the dimensions of the members defining the large force beams 44 and the small force beams 46 defining the annular elements 42 of the stent 20, can be modified. One presently preferred manner of modifying the members is to reduce the cross-sectional profile of the peaks 36, 38 between the small force beams 46, though the cross-sectional profile on the peaks 38 of the large force beams 44 could similarly be increased. It has further been suggested that since the members defining the annular elements 24 tend to bend according to a cantilever beam theory, a height 60 (see FIG. 5) of the members at the peaks 36, 38 between the small force beams 46 is reduced. Such a reduction in height 60, allows the peaks 36, 38 of the small force beams 46 to deflect more easily in response to an applied load.

Accordingly, in response to an intermediate, lower magnitude force $F_I$, 64, the peaks 36, 38 between the small force beams 46 begin to open while the peaks 36, 38 defining the large force beam 44, open to a lesser extent. As the peaks 36, 38 of the small force beam deflect, the circumferential dimension of the device lengthens. With lengthening, the moment arm becomes less orthogonal to the applied force and as the angle of deflection increases, the effective force component that operates to open the beams decreases as part of a cosine function. At a critical point, the elastic resistance inherent in the material of the beams 46 matches the effective force component and deflection ceases. There can exist a desired overlap such that the peaks 36, 38 between the large force beams 44 begin to bend before the elastic resistance inherent in the material defining the peaks 36, 38 between the small force beams 46 matches the effective force component applied to the stent 20. In this alternative approach, the large force beams 44 can open at some lesser rate than the expansion of the small force beams 46.

Once the deflection of the small force beams 46 cease in response to an intermediate force $F_I$, 64, a first stage of expansion has been accomplished. It is significant that when the stent 20 reaches this first stage of expansion, the forces being subsequently applied by the balloon have a relatively smaller longitudinally directed force component 94 (see FIG. 9). As stated, by minimizing the exposure of the stent to relatively larger longitudinal directed forces 94, stent shortening can be reduced. The stent establishes a partially deployed equilibrium at the intermediate pressure.

Next, as the forces being generated by the expansion of the balloon 80 increases to a higher magnitude $Fe_{68}$ 68, the large force beams 44 begin (or continue) to open. When this occurs, the stent 20 continues to expand to a desired diameter, one that is suited to effect the repair of the vessel.

Such staged expansion has the added benefit of minimizing the possibility of trauma to a vessel wall that may be inherent in uncontrolled expansion. That is, by employing staged expansion, the forces transmitted between the stent 20 and vessel wall can be reduced since such forces are dependent upon the acceleration of the expansion of the stent and resultant impact of the stent 20 with the vessel wall. Thus, by minimizing the acceleration of the expansion of the stent 20 of the present invention, forces transmitted by the same are reduced. Also, the same allows for relocation of stent at intermediate deployment stage.

Figure 12:
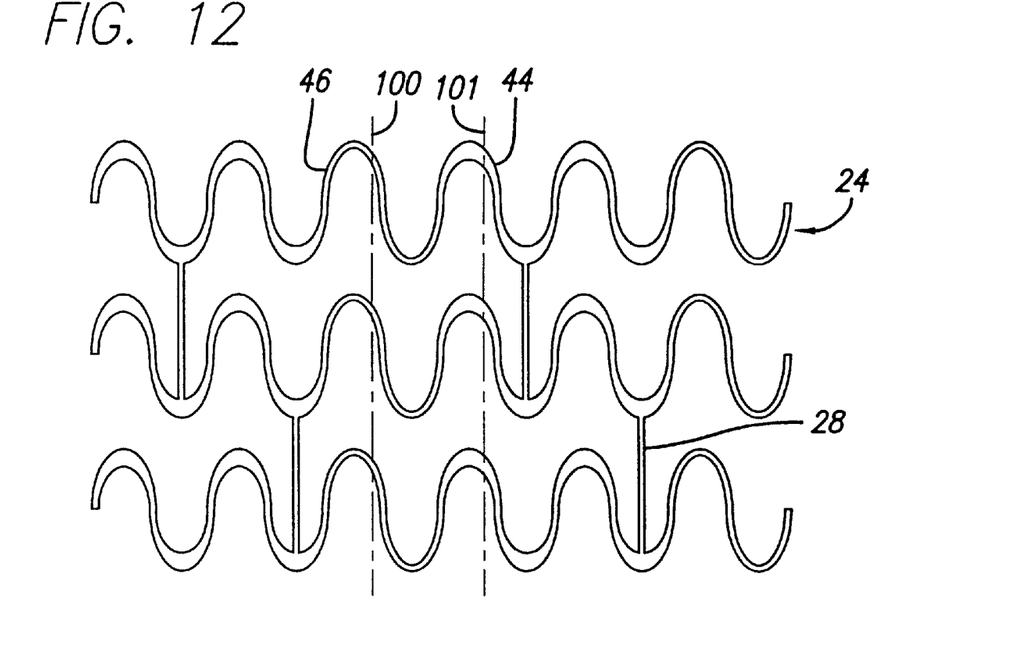
FIG. 12 is a side view of a second embodiment, depicting a series of annular elements in a sectioned and flattened state.

Referring now to FIG. 12, there is shown a second embodiment of a medical device of the present invention embodying an alternating pattern of high force beams 44 and low force beams 46 configured to form an annular element 24. A series of annular elements 24 are interconnected by struts 28. The low force beams are arranged so that they fall along the same longitudinal line 100. The high force beams 44 are also aligned to a common longitudinal line 101. When a low force is applied, the low force beams 46 will deflect an equal amount. The alignment of the beams ensures that the rings will deflect equally and uniformly.

Figure 13:
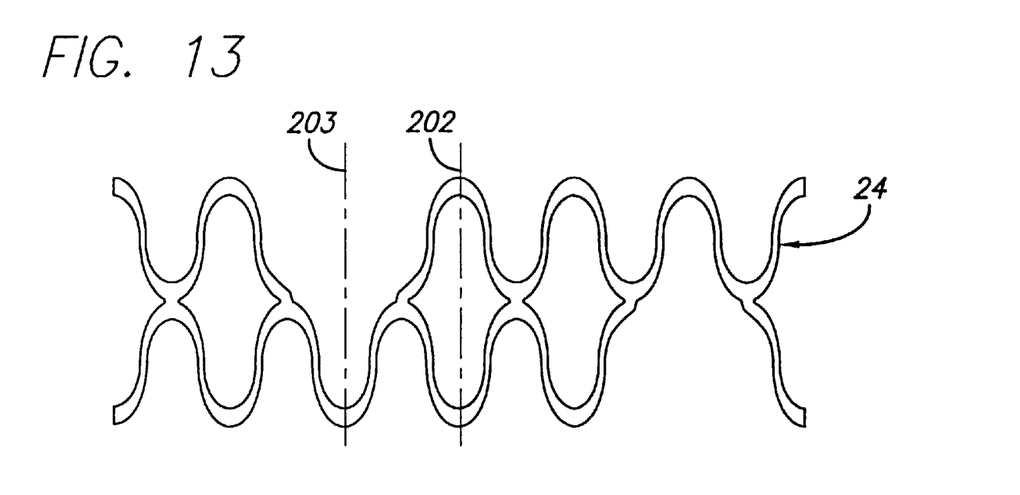
FIG. 13 is a side view of a third embodiment, depicting a series of annular elements in a sectioned and flattened state.

Turning now to FIG. 13, there is shown an unrolled stent annular element 24 with a diamond pattern which defines a third embodiment of the present invention. To achieve this pattern, beam elements of the diamond pattern are selectively removed. Two or more sinusoidal patterns of beams are cojoined at certain points to create a repeating diamond pattern 202. Beam elements can be selectively removed to form interrupted diamond patterns 203. The complete diamond patterns are in essence, high force beams. The incomplete diamond patterns are low force beams. The high force beams require a greater force to deflect an equivalent amount that low force beams. Even though all beams have equivalent geometry and bending stiffness, the varied number of beams serve to create regions of high force resistance 202 and low force resistance 203.

Figure 14:
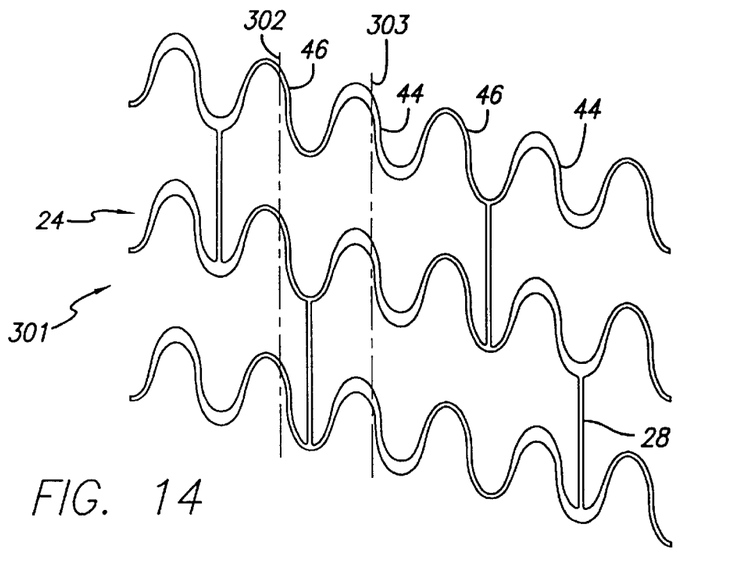
FIG. 14 is a side view of a fourth embodiment, depicting a series of annular elements in a sectioned and flattened state.

With reference to FIG. 14, an unrolled view of a fourth embodiment of a stent pattern that consist of a helical series of beams constructed in a sinusoidal pattern is shown. The sinusoidal pattern can form a helix 301. A single helix can form the stent rather than a multitude of distinct annular elements. At various locations, struts 28 can interconnect portions of the helix. The sinusoidal pattern is formed of a repeating pattern of high force beams 44, and low force beams 46. The high force and low force beams are arranged so that they fall along the same longitudinal line 302 and 303, to thereby facilitate alignment.

Figure 15:
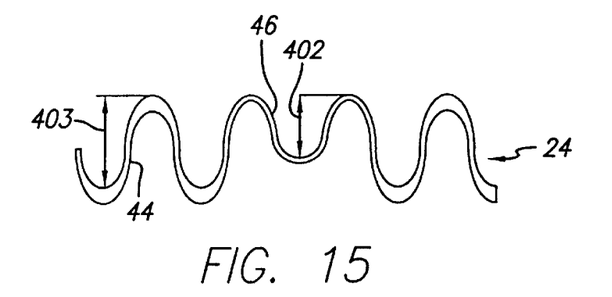
FIG. 15 is a side view of a fifth embodiment, depicting a series of annular elements in a sectioned and flattened state.

FIG. 15 depicts an unrolled view of a small amplitude, low force beam arrangement a fifth embodiment of the present invention, that is 2 wavelengths long and that defines a serpentine pattern. The low force beams 46 have a small amplitude 402. The high force beam 44 has a large amplitude 403. At a given low force $F_I$ 64 (See FIG. 6), the low force beam 46 will deflect until it is almost entirely in line with the vector of the force $F_I$ 64. Beyond this deflection, it is very difficult to achieve additional deflection in the low force beam 46. Rather, the high force beam 44 is the region of most additional deflection. Once the stent is in the final expanded state, the resistance of the annular element 24 to the collapsing forces of the stenosis are well opposed. The low force beams 46 in their straightened configuration can carry high columnar loads without deflection.

Figure 16:
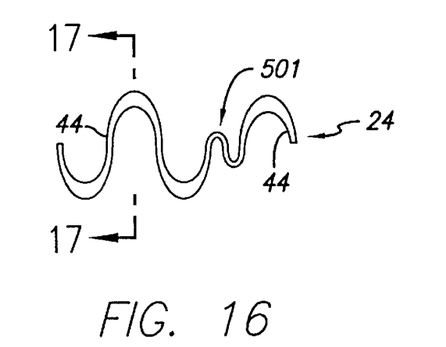
FIG. 16 is a side view of a sixth embodiment, depicting a series of annular elements in a sectioned and flattened state.
Figure 17:
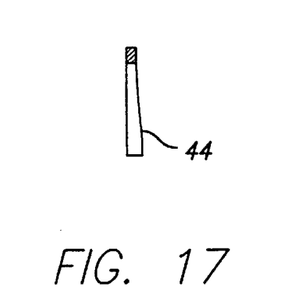
FIG. 17 is a cross-sectional view taken along lines 17—17 of FIG. 16.

In a sixth embodiment of the present invention (FIGS. 16 and 17), it is contemplated that the stent pattern include a small amplitude, one wavelength, low force beam arrangement 501 located at the inflection point of a large force beam 44. Additionally, this embodiment may further include beams of varying thickness (See FIG. 17).

Figure 18:
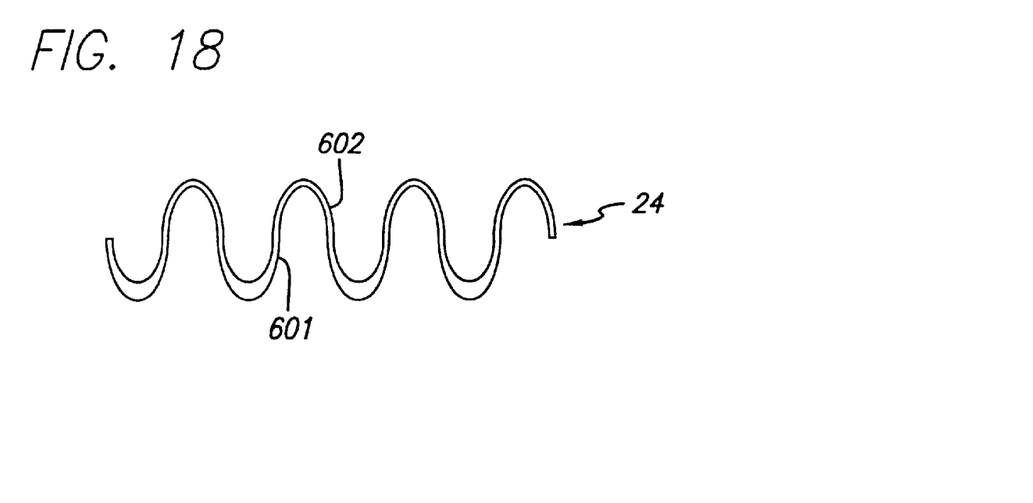
FIG. 18 is a side view of a seventh embodiment, depicting an annular element in a sectioned and flattened state.
Figure 19:
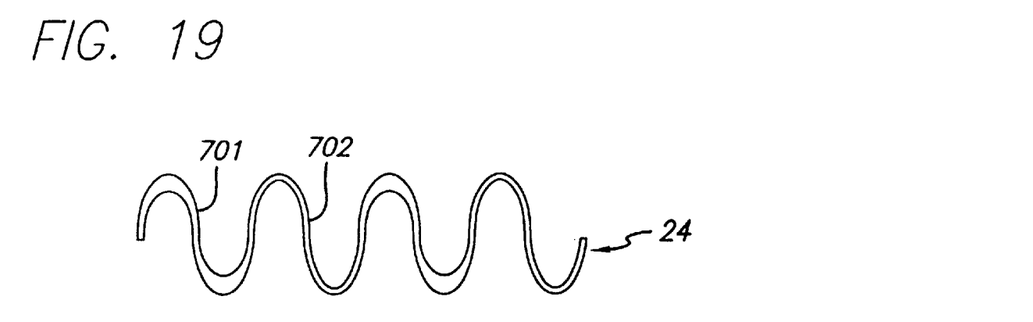
FIG. 19 is a side view of an eighth embodiment, depicting an annular element in a sectioned and flattened state.
Figure 20:
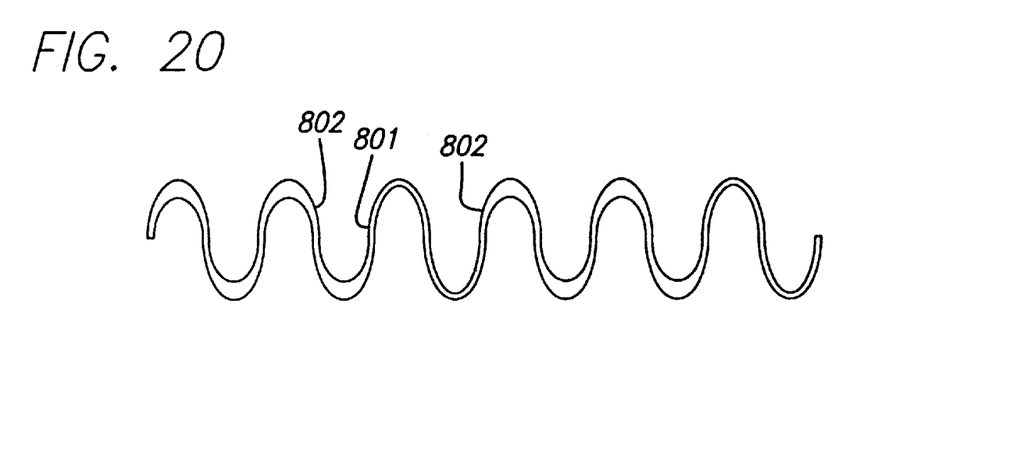
FIG. 20 is a side view of a ninth embodiment, depicting an annular element in a sectioned and flattened state.

In other embodiments of the present invention (FIGS. 18–20), the beams defining the annular elements can be varied in a number of ways. For example, the stent pattern can be defined by a sinusoidal pattern of alternating high force 601 and low force 602 beams (FIG. 18), alternating one wavelength high force beams 701 and low force beams 702 (FIG. 19), or a sinusoidal pattern with one low force beam 801 per each two high force beams 802 (FIG. 20).

The stent of the present invention therefore includes structure that is specifically adapted to minimize the effect of the opposing forces typically applied by expandable members of the delivery catheter. Such structure facilitates the stage expansion of the stent to thereby reduce stent shortening and trauma to a vessel wall.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A medical device, comprising:
    a generally tubular body defined by at least one annular element, said body having a first end and a second end; and
    said annular element including a first deformable portion having a first cross-sectional profile characterized by having a first mass and a second deformable portion having a second cross-sectional profile characterized by having a second mass that is larger than the first mass, said first deformable portion being more easily deformed than said second deformable portion and said first and second deformable portions each having a substantially completely deformed configuration, said annular element capable of assuming a partially enlarged and a substantially fully enlarged configuration;
    wherein upon application of a radially directed load of a first magnitude, said first deformable portion deforms into said substantially completely deformed configuration such that said annular element assumes its partially enlarged configuration prior to deformation of said second deformable portion.

2. The medical device of claim 1, wherein said second deformable portion deforms upon application of a radially directed load of a second magnitude to thereby facilitate said annular element to assume said substantially fully enlarged configuration.

3. The medical device of claim 2, wherein applying loads of said first and second magnitudes accomplishes a staged expansion of said medical device.

4. The medical device of claim 3, wherein said staged expansion operates to provide controlled expansion of said medical device to thereby reduce an impact with a wall defining the vasculature by decreasing forces transmitted from said medical device to the wall.

5. The medical device of claim 1, said annular element further comprising at least one additional deformable portion that deforms in response to separate and distinct radially directed loads of different magnitudes.

6. The medical device of claim 1, wherein said annular element is defined by an undulating pattern.

7. The medical device of claim 1, wherein said annular element includes a pair of first small force beams and a pair of second large force beams.

8. The medical device of claim 7, wherein there is a plurality of each of said pair of small and large force beams.

9. The medical device of claim 8, wherein a pair of said small force beams is interspersed between two of said large force beams.

10. The medical device of claim 8, wherein there are two pairs of said small force beams.

11. The medical device of claim 8, wherein there are two pairs of said large force beams.

12. The medical device of claim 7, wherein said pairs of small force beams define a first peak and said pair of large force beams define a second peak.

13. The medical device of claim 12, wherein:

said first peak has a first cross-sectional profile, said first cross-sectional profile having a first thickness and a first width; and said second peak has a second cross-sectional profile, said second cross-sectional profile having a second thickness and a second width.

14. The medical device of claim 13, wherein said first width is less than said second width.

15. The medical device of claim 13, wherein said first and second cross-sectional profiles are rectangular in shape.

16. The medical device of claim 1, wherein there are two or more of said annular elements.

17. The medical device of claim 16, further comprising longitudinally extending members connecting adjacent annular elements.

18. The medical device of claim 16, wherein:

said medical device is adapted for use with a delivery catheter having an expandable portion, said expandable portion capable of applying opposing forces to said first and said second ends of said body; and said first deformable portion and said second deformable portion cooperate to offset said opposing forces.

* * * * *